United States Patent [19]

Clark, Jr.

[11] E Patent Number: Re. 33,451

[45] Reissued Date of Patent: Nov. 20, 1990

[54] ARTIFICIAL BLOOD AND OTHER GAS TRANSPORT AGENTS

[75] Inventor: Leland C. Clark, Jr., Cincinnati, Ohio

[73] Assignee: Children's Hospital Medical Center, Cincinnati, Ohio

[21] Appl. No.: 758,201

[22] Filed: Jul. 23, 1985

Related U.S. Patent Documents

Reissue of:

[64] Patent No.: 4,443,480
Issued: Apr. 17, 1984
Appl. No.: 367,457
Filed: Apr. 12, 1982

[51] Int. Cl.[5] ..... A61K 31/16; A61K 31/025

[52] U.S. Cl. ..... 514/628; 514/755

[58] Field of Search ..... 514/628, 755

[56] References Cited

U.S. PATENT DOCUMENTS 3,194,840 7/1965 Berry .
3,547,995 12/1970 Bartlett .
3,600,415 8/1975 Sweeney et al. .
3,778,381 12/1973 Rosano et al. .
3,823,091 7/1974 Samejima et al. .
3,828,085 8/1974 Price et al. .
3,911,138 10/1975 Clark, Jr. .
3,962,439 6/1976 Yokoyama et al. .
3,993,581 11/1976 Yokoyama et al. .
4,041,086 8/1977 Moore et al. .
4,105,798 8/1978 Moore et al. .
4,220,606 9/1980 Moore .
4,461,717 7/1984 Moore .

OTHER PUBLICATIONS

Derwent Abstract J55147218—Describes Japanese Patent Publication No. 80/147218, Nov. 17, 1980 based on Japanese Appln. 80/46582 filed Apr. 9, 1980.

*Primary Examiner*—Sam Rosen
*Attorney, Agent, or Firm*—Wood, Herron & Evans

[57] ABSTRACT

Gas transport agents such as artificial blood containing a perfluorocyclocarbon and an amine oxide are disclosed. These compositions have been found to provide transparent emulsions or solutions for use in oxygen transport, particularly in animals. Large concentrations of perfluorocarbons may be employed even up to 50% or more by volume in preparing emulsions, microemulsions or solutions. The emulsions or solutions have been found to be very stable at room temperature storage conditions thereby providing significant advantages.

58 Claims, No Drawings

ARTIFICIAL BLOOD AND OTHER GAS TRANSPORT AGENTS

Matter enclosed in heavy brackets [ ] appears in the original patent but forms no part of this reissue specification; matter printed in italics indicates the additions made by reissue.

BACKGROUND OF THE INVENTION

A number of years ago, the oxygen carrying capacity and lack of toxicity of perfluorinated liquid were reported. Emulsions of fluorocarbon liquids were also used as artificial bloods. In brief, over nearly the last 20 years, considerable work has been accomplished in connection with the use of fluorocarbons and fluorocarbon emulsions as oxygen transfer agents and as artificial bloods. Artificial bloods are now being commercialized, particularly in foreign countries where the requirements for their use and commercialization are not as involved as they are here in the United States. It is inevitable that artificial blood will be commercialized and used throughout the world because of the significant need for such oxygen transport agents and the advantages of such agents over natural blood. U.S. Pat. No. 3,911,138 which issued to Leland C. Clark, Jr. sets forth the various advantages and needs for artificial blood and may be referred to as further background of this invention. In this Clark patent, artificial bloods containing perfluorocyclocarbons were disclosed as useful blood substitutes. Emulsions containing emulsified particles of the perfluorocyclocarbons were also infused intravenously into experimental animals and functioned as oxygen-carbon dioxide carrying agents intravascularly. Furthermore, the perfluorocyclocarbons surprisingly were found to be excreted from the animal body through the tissue, particularly the lungs and skin. The perfluorocyclocarbons disclosed in this Clark patent were referred to as RES-phobic, which indicated that the perfluorocyclocarbons exhibited a unique property of temporary sequestration by the liver or spleen and subsequent elimination by the animal body. It was later disclosed in U.S. Pat. No. 4,105,798 which issued to Leland C. Clark, Jr. et al that certain other perfluoro polycyclic compounds were useful as synthetic blood and perfusion media. The perfluorinated polycyclic compounds disclosed in this patent are known generally as bicyclononanes and adamantanes. Bicyclononanes and adamantanes were found to have a high oxygen solubility, very low body residue, formed very stable emulsions and had a very satisfactory vapor pressure enabling them to be excellent candidates for blood substitutes and perfusion compounds.

Thus, emulsions made from perfluorocyclo compounds such as perfluorodecalin have been found useful as blood substitutes because the cyclic fluorocarbon is transpired by the body through the skin and the lungs. However, in order for these emulsions to be preferred for biological use, they must be freshly prepared because they are not stable. That is, they tend to increase in opacity and the particle size of the fluorocarbon liquid increases rather rapidly with time. This process can be slowed by cooling or even by freezing. Whereas perfluorinated organic amines such as perfluorotributylamine or perfluorotripropylamine will make emulsions having good stability, it is known that such compounds tend to reside in the body, for example the liver or spleen, for considerable periods of time in comparison to the perfluorocyclo compounds such as perfluorodecalin. Recently, therefore, perfluorodecalin and perfluorinated amines such as perfluorotripropylamine have been combined in order to provide an emulsion which has increased stability and which would leave the body at a reasonable rate. Nevertheless, it has been observed that such perfluoroamines as tripropylamine tend to leave the body only very slowly and still such emulsions must also be kept cold or even frozen. Thus, while these compositions attempt to combine perhaps the best properties of both the fluorocarbons employed, namely, perfluorodecalin and perfluorotripropylamine, there are still problems that remain. Nevertheless, these preparations have been employed fairly widely in human beings in life saving procedures and have been proven to be very useful. Therefore, these advances, together with considerable research to date serve to emphasize that highly fluorinated organic compounds in the form of emulsions are very useful in supporting life when used in place of whole blood.

The stability of an emulsion particle in a fluorochemical emulsion has great importance in the sense that the greater the stability, the longer the emulsion can be safely stored before it is used in vivo. In addition, if the emulsion is very stable, it can be stored without refrigeration, a factor of great importance in its possible use as an oxygen transport agent or as an artificial blood for civilian and military purposes, especially in countries where there is little or no refrigeration. Furthermore, a stable emulsion is more predictable from medical standpoints rather than one which tends to deteriorate with time. Normally, after administration to an animal, an emulsion is exposed to body temperatures and this is a factor which may increase its conversion to larger particles. Much remains to be learned about the factors working for and against particle stability in the blood stream and tissues of mammals. While it seems reasonable to suppose that factors which would make for an in vitro stability also make for in vivo stability, there are also special considerations involved in promoting in vivo stability of foreign particles such as perfluorochemical particles. All of the above points to the need for improvements in oxygen transport agents and artificial bloods.

SUMMARY OF THE INVENTION

This invention is directed to gas transport agents and those agents especially suited for artificial bloods. The agents of this invention contain perfluorocyclocarbon compounds and organoamine oxides. In one feature of this invention, room temperature stable mixtures of perfluorocyclocarbons and water have been obtained by the incorporation of an organoamine oxide as a surfactant or solubilizing agent. Even room temperature stable emulsions or solutions have been prepared which have the property of transparency. While these mixtures may either be considered a solution, a micellar solution, microemulsion, vesicular suspension, emulsion or a mixture of all of these physical states, it nevertheless has been demonstrated that in preferred embodiments of this invention such liquids are room temperature stable for extended periods of time.

It has also been found that astonishingly large concentrations of perfluorocyclocarbons are obtained in aqueous solutions or emulsions, even up to concentrations of 50% or more perfluorocyclocarbon by volume or 95% by weight in water. The combination of the perfluorocarbon and organoamine oxide surfactant or solubilizing agent seems to synergistically behave in water. In the past, usually 10 or 20 or at most 30% by volume perfluorocarbon liquids were considered to be concentrated emulsions. Moreover, the concentrated emulsions or solutions of this invention even have room temperature stability without any visible change for many months.

Nearly transparent or transparent emulsions or solutions of perfluorinated compounds in water have also been surprisingly obtained. Such transparency has been achieved with very little sonication and such solutions or emulsions have room temperature stability for many months. Compositions of this invention containing perfluorocyclocarbon compounds and organoamine oxides as surfactants or emulsifying agents in water offer excellent properties as oxygen transport agents. They are relatively non-toxic and non-hemolytic which renders them suitable for use as artificial bloods. Even though considerable amounts of perfluorocarbon may be concentrated in water, it has been found that the viscosities of the resultant fluids are very satisfactory for use as artificial bloods. The viscosities are near the viscosity of water. Furthermore, it has been discovered that the mixture, i.e., emulsions or microemulsions or whatever the physical or chemical state thereof, would pass readily at low pressures through a 0.22 micron filter which indicates that they will traverse the capillaries of living tissue, thus, such discovery is significant for biological and medical applications. This technique can be used to sterilize the mixtures as well. In contrast, previously known emulsions would only partially pass through such a filter at high pressures and thus such emulsions must be autoclaved for sterilization. Upon infusion into animals, the emulsions or solutions function as oxygen transport agents. Furthermore, the perfluorocyclocarbons employed have been proven to leave the body and have RES-phobic properties which have heretofore been characterized in the earlier patents mentioned in the background of this invention. The emulsifier itself is excreted by the kidney and not retained in the body.

Previous experience with perfluorinated derivatives such as FC-47 has demonstrated that emulsions of about 10 to about 30% by volume would increase in viscosities as the concentrations increased. These emulsions would tend to have the consistency of honey at the higher concentrations. In comparison, even with concentrations on the order of 50% or more by volume of perfluorocyclocarbons, particularly DAWN, containing the amine oxide, tend to have viscosities approaching the viscosity of water. These results are remarkably surprising. In brief, these and other advantageous properties of the compositions and methods of this invention will be further understood with reference to the following detailed description.

DETAILED DESCRIPTION OF THE INVENTION

The gas transport agents or artificial blood compositions of this invention are liquids. The terms "liquids", as used herein, is a comprehensive designation including any components in a fluid. As stated above, the physical state of the liquids may vary and include solution, miscellar solution, microemulsion, vesicular suspension, emulsion, or mixtures of any of these. In certain preferred features, as developed above, transparent solutions, emulsions, microemulsions, mixtures or other states, have been surprisingly found to exist wherein the [perfluorocarbon] *perfluorocyclocarbon* is mixed with water in the presence of an organoamine oxide surfactant or solubilizing agent, as the case may be. The term "perfluorocyclocarbon" means a cyclic compound of carbon, whereas the term "substituted derivatives thereof" characterizes substituted perfluorocyclocarbons with acyclic or alkyl side chains, preferably lower alkyl side chains. It should also be noted that the term "perfluorocyclocarbon" denotes substitution of all hydrogen atoms attached to the carbon atoms chain or ring and any carbon side groups with fluorine. It is conceivable in the manufacture of such compounds that minor amounts of substantially fluorinated derivatives may be mixed with completely fluorinated compounds. This is permissible providing the lack of complete replacement of all hydrogens does not affect the essential characteristics of the liquid perfluorocarbons of this invention, particularly when the active hydrogens critically enhance the toxicity of the compounds when they are employed in oxygen transport agents in animals. Among the perfluorocyclocarbons which may be employed are perfluorobicyclo[4.3.0]nonane, [perfluorotrimethylcyclohexane, perfluoroisopropylcyclohexane,] perfluoroendotetrahydrodicyclopentadiene, perfluoroadamantane, perfluoroexo-tetrahydrodicyclopentadiene, perfluorobicyclo[5.3.0]decane, [perfluorotetramethylcyclohexane, perfluoro-1-methyl-4-isopropylcyclohexane, perfluoro-n-butylcyclohexane,] perfluorodimethylbicycle[3.3.1.]nonane, perfluoro-1-methyl adamanatane, [perfluoro-1-methyl-4-t-butylcyclohexane,] perfluorodecahydroacenaphthene, perfluorotrimethylbicyclo[3.3.1.]nonane, perfluoro-n-undecane, perfluorotetradecahydrophenanthrene, perfluoro-1,3,5,7-tetramethyladamantane, perfluorododecahydrofluorene, perfluoro-1,3-dimethyl adamantane, [perfluoro-n-octylcyclohexane,] *and* perfluoro-7-methyl bicyclo[4.3.0.]nonane[, perfluoro-p-diisopropylcyclohexane, and perfluoro-m-diisopropylcyclohexane].

It is also to be understood that the fluorocarbons that are useful according to the principles of this invention may be generally termed "perfluorocyclocarbons" or "perfluorocarbocyclic compounds" or "cyclic perfluorocarbons". The term used predominantly in this description is perfluorocyclocarbon, however, the term cyclic perfluorocarbons or perfluorocarboncyclic compound are considered alternative expressions. The term "carbocyclic" or "cyclocarbon" means a homo-cyclic compound of carbon, i.e., a ring or rings of carbon atoms. The carbocyclic [compound may be moonocyclic as in the case of cyclohexane or bicyclic as in the case of naphthalene or polycyclic as in the case of phenanthrene. Furthermore, other polycyclic perfluoro compounds whose ring structure cannot be aromatized without destruction of its original carbon-to-carbon cyclic bonds are included. Thus, the later mentioned perfluorocompounds which may be employed in this invention are distinguished from the perfluorodecalin compounds mentioned above, or other similar compounds which can be aromatized.] *compounds according to this invention are derived from two classes. The first class of perfluorocyclocarbon compounds are non-aromatizable perfluorinated polycyclic compounds having 9–18 carbon atoms and at least two bridgehead carbon atoms linked through a bridge containing at least one carbon atom. By the term bridgehead carbon atom is meant a carbon atom bonded to three other carbons in a cyclic*

*compound having 2 or more rings. By the term "non-aromatizable" is meant a polycyclic perfluoro compound whose ring structure cannot be aromatized without destruction of its original carbon-to-carbon cyclic bonds. Thus, the perfluoro compounds of this invention are to be further distinguished from the perfluorodecalin above mentioned or other similar compounds which can be aromatized. This invention thus employs the perfluoro derivatives of such $C_9$–$C_{18}$ polycyclic compounds as bicyclononanes (e.g. bicyclo[3.3.1]nonane, 2,6-dimethylbicyclo[3.3.1]nonane or 3-methylbicyclo[3.3.1]nonane), adamantane, methyl and dimethyladamantane, and ethyladamantane. As hereinafter mentioned these compositions are described in U.S. Pat. Nos. 3,911,138 and 4,105,798 which are incorporated by reference at Column 5 lines 6–8. The second class of perfluorocyclocarbon compounds contain tricyclic perfluorocyclocarbons as in the case of phenanthrene and quadricyclic perfluorocyclocarbons as in the case of adamantane.* The carbon ring can be alkylated with a lower alkyl group or groups such as methyl or ethyl as in the case of perfluoro(methylcyclohexane) or perfluoro(-decahydrodimethylnaphthalene). Perfluorocyclocarbons of this invention may be formed of "neat" perfluorocarbon liquids or solids and often, due to their mode of manufacture, are mixtures of perfluorocyclocarbons. For instance, perfluoro-1,3-dimethyl adamantane is normally a solid but in mixture with perfluorotrimethylbicyclo[3.3.1.]nonane a liquid is formed and this mixture is sometimes referred to simply herein as "DAWN". The designation DAWN comprises these compounds in varying amounts or proportions as revealed by gas chromatography wherein a number of major and minor peaks are observed representing the isomers of perfluoro-1,3-dimethyl adamantane and perfluorotrimethylbicyclo[3.3.1.]nonane. Gas chromatography results are exhibited later in TABLE II. Perfluorocyclo compounds of the type suitable for use in this invention are disclosed in U.S. Pat. Nos. 3,911,138 and 4,105,798 mentioned above and these patents are incorporated herein by reference.

The following TABLE I lists certain presently preferred perfluorocarbon liquids.

TABLE I

| TRADE NAMES | CHEMICAL NAMES | EMPIRICAL FORMULA | MOLECULAR WEIGHT | BOILING POINT | VAPOR PRESSURE torr | SPECIFIC GRAVITY | REFRACTIVE INDEX |
|---|---|---|---|---|---|---|---|
| PP9 | perfluoro(1-methyl-decalin) | $C_{11}F_{20}$ | 512 | 160° C. | 5.2 (37.5° C.) | 1.9720 | 1.299 at 23° C. |
| DAWN | perfluoro(1,3-dimethyl adamantane) | $C_{12}F_{20}$ | 524 | 176° C. | 2.7 (37.0° C.) | — | — |
| | perfluorotrimethyl-bicyclo[3.3.1.]nonane | $C_{12}F_{22}$ | 562 | 177° C. | 2.5 (37.0° C.) | 2.0250 | 1.3338 at 20° C. |

The above perfluorocarbons are capable of being synthesized by either well known chemical or electrochemical processes. The chemical processes yield fairly pure substances of known structure, having well defined boiling points. Whereas the electrochemical processes tend to yield a mixture of isomers, the liquids have well defined boiling points. With respect to gas chromatography, each liquid is capable of being well defined by either the packed or capillary column procedure. The standard to define each compound in gas chromatography is prepared as follows: 2 microliters of neat liquid are added to 120 milliliters of air in a sealed bottle and allowed to vaporize producing a stock standard; upon vaporization, 120 microliters of the vapor from the stock standard are added to another 120 milliliters of air in a sealed bottle producing the working standard; the sample measured by the procedure is withdrawn from the working standard, thus, a typical sample will contain 16.7 pico liters of perfluorocarbon per milliliter of standard; however, in the capillary column procedure, the sample is split into a ratio of 23:1, therefore, only 1/23 of the sample is actually measured. As indicated in Table II, the retention time is highly definitive of each liquid used in this invention. Moreover, the capillary procedure is more specific than the packed column procedure by defining additional characteristic peaks of each compound. Thus, a more precise definition of compounds can be had with the capillary column procedure.

TABLE II

| | Gas Chromatography* | |
|---|---|---|
| | Packed Column** | Capillary Column*** |
| Set Up | | |
| Standard | [16.7 pl/ml]**** | [16.7 pl/ml]**** |
| Recorder Sensitivity | 0.001 v full scale | 0.001 v full scale |
| Column Temperature | 100° C. | 37° C. |
| Detector Temperature | 250° C. | 250° C. |
| Injector Temperature | 150° C. | 150° C. |
| $N_2$ Gas Flow | 40 ml/min | 40 ml/min |
| Split | — | 23:1 |
| Recorder Speed | 2.5 cm/min | 2.5 cm/min |
| Compounds | | |
| (1) PP9 (perfluoro 1-methyldecalin) | | |
| Attenuation | 8 | 4 |
| Sample | 50 mcl | 100 mcl |
| Peaks | 3 | 7 |
| Retention Time | | |
| $Peak_1$ | 52 mm | 88 mm |
| $Peak_2$ | 57 mm | 100 mm |
| $Peak_3$ | 82 mm | 142 mm |
| $Peak_4$ | — | 151 mm |
| $Peak_5$ | — | 158 mm |
| $Peak_6$ | — | 163 mm |
| $Peak_7$ | — | 168 mm |
| (2) DAWN (perfluoro 1,3-dimethyladamantane and perfluorotrimethylbicyclo-[3.3.1.]nonane) | | |
| Attenuation | 8 | 8 |
| Sample | 10 mcl | 100 mcl |
| Peaks | 1 | 5 |
| Retention Time | | |
| $Peak_1$ | 115 mm | 269 mm |
| $Peak_2$ | — | 294 mm |
| $Peak_3$ | — | 300 mm |
| $Peak_4$ | — | 304 mm |
| $Peak_5$ | — | 313 mm |

*Antek 300 Gas Chromatography instrument equipped with Ni63 electron capture detector

**Supelco, Inc. Packed Column

***Scientific Glass Engineering Capillary Column

****pl/ml = picoliters/milliliter

The above perfluorocarbons all have in common a high solubility for oxygen and carbon dioxide, inertness, and RES-phobic properties, as developed above. One main property generic to the preference of the fluorocarbons according to this invention over the other fluoro-containing compounds is their chemical structure rendering them RES-phobic. As developed in the background of this invention. RES-phobic fluorinated liquids tend to accumulate in the bodies of animals, principally in the liver, and to a lesser extent in the spleen and the kidneys but leave in an acceptable period of time. This is significant because such liquids will not become fixed indefinitely within the cells of an organ. A perfluorocyclocarbon or a mixture thereof is preferably employed having a vapor pressure within the range of about 1 to about 25 torrs at about 35° C. Thus, such liquids or mixtures are not only RES-phobic, but upon escaping the cell expediently, they will not cause adverse gas collection in the tissue of animals.

The term "organomine oxide" is a generic expression to define cyclic or acyclic amine oxides and substituted derivatives thereof. The term "organo" is intended to cover in its broadest sense acyclic as well as carbocyclic organic moieties whether they contain within their structure other atoms such as oxygen, bromine or nitrogen, or have substituted groups or side chains. In a preferred aspect of this invention, the organoamine oxides are fluorinated or polyfluorinated organoamine oxides. Organoamine oxides of the broad class which may be suitable for use in this invention are described in a general way in U.S. Pat. Nos. 3,194,840; 3,547,995; 3,600,415; 3,778,381 and 3,828,085. A detailed discussion of organoamine oxides or N-oxides appears in the literature reference "The Pharmacology and Biochemistry of N-Oxides", Pharmacological Reviews, Vol. 21, No. 4, 1969 pp. 325–355, by M. H. Bickel. At present, there is believed to be no reason to exclude compounds from this broad class of amine oxides described in these patents because it is believed that the broader aspects of this invention include the use of an organic compound having an amine oxide group. Thus, the disclosures of the amine oxides in the mentioned patents are included herein by reference so that a person of ordinary skill will understand the intended scope of the invention in this regard. It should also be pointed out that certain of the amine oxides such as amidoamine oxides have been suggested as surfactants in perfluorinated hydrocarbon transport agents of the type disclosed in the 1968 edition of J. C. Norman, Organ Perfusion and Preservation, referred to in U.S. Pat. No. 3,828,085. However, it has not been heretofore suggested or appreciated that amine oxides may be employed with perfluorocyclocarbon compounds in water to form advantageous oxygen transport agents, let alone having the further advantageous and unexpected properties of the compositions of this invention as understood in view of the entirety of this description. In an especially preferred form of the invention, a fluoroamidoamine oxide is employed, in particular, having the formula:

$$C_3F_7O(CF_2)_3\overset{\overset{\displaystyle O}{\|}}{C}NH(CH_2)_3\underset{\underset{\displaystyle O}{\downarrow}}{N}(CH_3)_2.$$

Hereinafter this compound will be referred to sometimes as "XMO10".

The invention will be further understood with reference to the following detailed Examples which illustrate its practice and such examples are not considered to be limiting.

EXAMPLE 1

Two grams of XMO10 were dissolved in 200 ml of sterile distilled water. Nine ml of this 1% (w/v) XMO10 solution was added to 1 ml of DAWN fluorocarbon liquid and sonicated for 10 seconds using a Branson sonicator. The resultant solution was clear and transparent and had a slight pink or bluish cast in certain lights.

A mouse with a weight of 25.6 grams was injected with 1 cc of DAWN/XMO10 emulsion which is equivalent to a dose of 39.0 cc/kg. The mouse remained in good health.

EXAMPLE 2

One cc of the 1% XMO10 preparation of Example 1 was diluted with 9 cc of distilled water, thereby resulting in a concentration of 0.1% XMO10. One cc of DAWN was combined with 9 cc of the 0.1% XMO10 mixture. When 1 cc of DAWN was added to the XMO10 mixture, one could not see any change in the layers. Whereupon, after sonicating for approximately 20 seconds, the emulsion was warm and cloudy. It reverted to a clear solution or emulsion when cooled. A mouse was injected with 1 cc intravascularly as in Example 1.

EXAMPLE 3

Other emulsions prepared in the fashion as in Examples 1 and 2 were made and even after over one year the emulsions are still transparent, or nearly so, and do not appear to have changed chemically after being kept at room temperature. Furthermore, other mice that have been injected with doses on the order of those identified in Examples 1 and 2 were still in good health and showed only the slightest traces, if that, of fluorocarbons according to gas chromatographic with electron capture detection techniques which can measure as little as $2\times10^{-15}$ liters in samples of whole-body transpired air. In comparison, of course, large amounts of other fluorocarbons such as F-tributylamine and even measurable amounts of F-tripropylamine as developed in the background of this invention still remain after one year. It has also been found that the emulsions of XMO10 and DAWN can be heated and cooled repeatedly with the emulsion becoming more transparent while cold and with the system completely reversible. Thus, this also demonstrates the stability of these unique emulsions.

EXAMPLES 4–13

A series of 10 ml test tubes were set up containing 50% by volume of perfluorocarbon liquids identified in Table III hereinafter and 50% by volume of a 2% (2 grams of XMO10 in 100 cc water) water solution of XMO10. The mixtures were sonicated and the results are reported in the Table.

TABLE III

| Example No. | Compound | 10 Min. after gentle mixing | | Optical Density after sonication | | |
|---|---|---|---|---|---|---|
| | | Upper | Lower | Initial | 7 days | 9 weeks |
| 4 | FC47 | Clear | Turbid | 32 | 33 | 32 |

TABLE III-continued

| Example No. | Compound | 10 Min. after gentle mixing | | Optical Density after sonication | | |
|---|---|---|---|---|---|---|
| | | Upper | Lower | Initial | 7 days | 9 weeks |
| 5 | PP5 | Clear | Turbid | 8.0 | 8.5 | 9.3 |
| 6 | PP9 | Clear | Turbid | 6.0 | 6.0 | 6.0 |
| 7 | FC80 | Clear | Turbid | 56 | 58 | 72 |
| 8 | PID | Clear | Turbid | 79 | 78 | 75 |
| 9 | PIID | Clear | Turbid | 52 | 54 | 52 |
| 10 | E3 | Clear | Turbid | 69.3 | 68 | 66 |
| 11 | E4 | Clear | Turbid | 57 | 58 | 57 |
| 12 | DAWN | Clear | Clear | 0.06 | 0.26 | .11 |
| 13 | PFOB | Clear | Turbid | 16 | 18 | 21.5 |

With reference to Table III, with the exception of DAWN and XMO10, both of which have been identified above, the following perfluoro chemicals are identified: perfluorotributylamine (FC47), perfluorodecalin (PP5), perfluoro 1-methyldecaline (PP9), perfluorotetrahydrofuran (FC80), perfluoroether (PID) $[(CF_3)_2CFOCF_2(CF_2)_2CF_2OCF(CF_3)_2]$, perfluoroether (PIID) $[(CF_3)_2CFOCF_2(CF_2)_6CF_2OCF(CF_3)_2]$, perfluoropolymer (E3)

$[CF_3CHF(OCF_2\overset{CF_3}{\overset{|}{C}}F)_2OCF_2CF_2CF_3]$, perfluoropolymer (E4)

$[CF_3CHF(OCF_2\overset{CF_3}{\overset{|}{C}}F)_3OCF_2CF_2CF_3]$, octyl bromide (octyl br), and perfluoroetherpolymer (Fomblin Y/01).

Astonishingly, even with a concentration of 50% by volume perfluorocarbon liquid, the DAWN/XMO10 liquid was a nearly transparent emulsion or solution which was obtained almost without any sonication. The DAWN/XMO10 preferred composition of this invention remained without visible change for several months. All of the other perfluorocarbons tested according to Table III formed milky emulsions which were vastly different in appearance. Other emulsions or solutions of DAWN and XMO10 made at other times were also transparent and showed similar stabilities. The structure of XMO10 which was identified above was analyzed to verify its chemical constituents.

EXAMPLES 14–78

The table of data which follows further illustrates the principles of this invention in comparison to other perfluorocarbons. The prefix "F" means perfluorinated. The fluorocarbon was by volume or weight where a solid was employed. The % XMO10 was by weight-/volume of water as in the earlier examples. The optical density was determined at 540λ at room temperature. At the end of a brief sonication of about 10–90 seconds, an initial determination of optical density was made (Min.) and a later determination (Max.) was made after a number of days as indicated in TABLE IV. The other commercial designations have been identified above, as well as DAWN.

TABLE IV

| EMULSION | | | OPTICAL DENSITY | | | |
|---|---|---|---|---|---|---|
| % Fluorocarbon ml/100 ml | Fluorocarbon | % XMO10 w/v | Range Initial | Min. | Max. | Time (Days) |
| 10% | F-1-methyl-4-t-butylcyclohexane | 2% | 0.90 | 0.90 | 1.50 | 81 |
| 10% | F-tetramethylcyclohexane | 2% | 1.70 | 1.70 | 2.80 | 81 |
| 10% | F-m-diisopropylcyclohexane | 2% | 2.00 | 2.00 | 3.20 | 49 |
| 10% | F-p-diisopropylcyclohexane | 2% | 2.30 | 2.10 | 4.20 | 49 |
| 10% | F-trimethylcyclohexane | 2% | 0.55 | 0.55 | 9.60 | 81 |
| 10% | F-n-butylcyclohexane | 2% | 7.00 | 7.00 | 12.50 | 49 |
| 10% | F-isopropylcyclohexane | 2% | 5.00 | 5.00 | 15.00 | 49 |
| 10% | F-dimethylcyclohexane | 2% | 1.00 | 1.00 | 33.00 | 81 |
| 10% | F-kerosine (low boiling) | 2% | 12.60 | 12.60 | 20.75 | 99 |
| 10% | F-kerosine (high boiling) | 2% | 0.78 | 0.78 | 2.50 | 99 |
| 10% | F-tripropylamine | 2% | 10.00 | 10.00 | 27.00 | 99 |
| 10% | F-dimethylcyclohexylmethyl amine | 2% | 2.60 | 2.60 | 11.00 | 99 |
| 10% | F-n-ethylmorpholine | 2% | 10.50 | 10.50 | 62.00 | 99 |
| 10% | F-heptane (mixed isomers) | 2% | 21.00 | 21.00 | 48.00 | 99 |
| 10% | F-n-nonane | 2% | 6.20 | 6.20 | 21.00 | 102 |
| 10% | F-2,2,4,4 tetramethylpentane | 2% | 5.40 | 5.40 | 17.00 | 102 |
| 10% | F-isopropyl-4-bromobutylether | 2% | 6.60 | 6.60 | 20.00 | 90 |
| 10% | F-dimethylbicyclodecane | 2% | 0.80 | 0.80 | 1.90 | 120 |
| 10% | F-decalin | 2% | 1.30 | 1.00 | 8.40 | 175 |
| 10% | F-dimethyldecalin | 2% | 0.64 | 0.58 | 1.50 | 201 |
| 10% | F-dimethyladamanane/F-dimethylbicyclo-nonane(1:1) | 2% | 0.43 | 0.37 | 1.20 | 230 |
| 10% | DAWN | 2% | 0.025 | 0.02 | 0.075 | 229 |
| 5% w/v | F-adamantane | 2% | 0.82 | 0.82 | ~2.00 | 131 |
| 5% w/v | F-methyladamantane | 2% | 0.20 | 0.20 | 0.80 | 131 |
| 5% w/v | F-dimethyladamantane | 2% | 0.05 | 0.02 | 0.50 | 131 |
| 50% | DAWN | 2% | 0.04 | — | — | — |
| 50% | F-octylbromide | 2% | 25.00 | — | — | — |
| 50% | E-4 | 2% | 57.00 | — | — | — |
| 50% | E-3 | 2% | 69.50 | — | — | — |
| 50% | PIID | 2% | 52.00 | — | — | — |
| 50% | PID | 2% | 79.00 | — | — | — |
| 50% | FC-80 | 2% | 56.00 | — | — | — |
| 50% | F-decalin | 2% | 8.00 | — | — | — |
| 50% | F-methyldecalin | 2% | 6.00 | — | — | — |
| 50% | FC-47 | 2% | 33.00 | — | — | — |
| 10% | PID | 1% | 29.00 | 20.00 | 28.00 | 125 |
| 10% | PIID | 1% | 12.00 | 12.00 | 19.00 | 125 |
| 10% | F-bicyclodecane | 1% | 4.40 | 7.80 | 125 | |

TABLE IV-continued

| EMULSION | | | OPTICAL DENSITY | | | |
|---|---|---|---|---|---|---|
| % Fluorocarbon | | % XMO10 | Range | | | Time |
| ml/100 ml | Fluorocarbon | w/v | Initial | Min. | Max. | (Days) |
| 10% | F-decalin | 1% | 4.60 | 4.00 | 5.30 | 125 |
| 10% | F-dimethylbicyclononane | 1% | 2.60 | 2.60 | 4.30 | 125 |
| 10% | DAWN | 1% | 0.09 | 0.07 | 0.11 | 125 |
| 10% | F-dimethyldecalin | 1% | 1.50 | 1.40 | 2.10 | 126 |

The above tabulated data demonstrates quite clearly that extremely stable emulsions are prepared from perfluorocyclo derivatives in combination with an organoamine oxide and such stability exists for long periods of time in comparison to other perfluorocarbon liquids. Amounts of perfluorocarbon from about 10 to 50% and from about 1 to 10% XMO10 may be employed, and even as little as 1-2% to obtain substantially transparent mixtures. More particularly, the preferred DAWN composition exhibits a stability far exceeding the stability of any of the perfluorocarbons tested. The compositions are relatively non-toxic and non-hemolytic.

In connection with the measurement of optical density, it should be understood that optical density (2 minus the log of the transmission) is commonly used in colorimetry because there is usually a linear relation between inceasing optical density and increasing concentrations of a colored substance. In the data above, it is a measurement of the opacity of the solution or emulsion, or whatever the state may be. The smaller a particle, the more transparent the solution, emulsion or microemulsion, as the case may be, until a point where it is so transparent that it cannot be distinguished from water, for instance. The term "transmission" is not used much but it is easier to understand in a way because at 100% transmission (O.D.=2-log 100=2-2=0) the sample is water clear. If not completely transparent, the instrument is often set to read at 100% transmission and as color or opacity (like milk) is increased, the transmission decreases until it reached 0. At this point the optical density is 2-log of 0=2-0=2. To read the opacity of emulsions beyond this point, it is necessary to either dilute them or use a shorter light path than for instance a 1 cm light path. Because of the complications which may be introduced by dilution factors which may change particle size, it was preferred to use a shorter light path in determining the optical density. If a solution has an optical density of 1.7 in a 1 cm cell, it will have an optical density of 0.17 in a 0.1 cm cell. Hence, if 1.7 is measured in a 0.1 cm cell, the opacity density by this method becomes 17. It is practical to use a light path down to 0.05 cm or even to 0.01 cm in routine work in the laboratory. Therefore, optical density measurements reported in TABLE IV above were made with varying light paths and the results were mathematically made comparable. The compositions of this invention are especially useful as stated above for artificial blood. However, they also have utility as other oxygen or gas transfer agents in the body and for treatment of various conditions such as ischemia, shock, heart attack, stroke, and other such conditions where oxygenating the tissue is important. Further in the broadcast sense, other uses will become apparent for these liquids as gas transfer agents in view of their high solubility for oxygen, carbon dioxide and other gases. Furthermore, the capability of the perfluorocarbons employed above as gas transport agents in animals may be further understood by reference to the above patents cited in the description.

In view of the above detailed description, it will become apparent to a person of ordinary skill that other modifications may be made without departing from the spirit and scope of this invention.

What is claimed is:

1. A gas transport agent liquid composition containing a *tricyclic or quadricyclic* perfluorocyclocarbon and an organoamine oxide.

2. The composition of claim 1 wherein said oxide is a fluoroorganoamine oxide.

3. The composition of claim 1 wherein said oxide is a polyfluoroamidoamine oxide.

4. The composition of claim 3 wherein the oxide is defined by the formula $$C_3F_7O(CF_2)_3\overset{\overset{\displaystyle O}{\|}}{C}NH(CH_2)_3\underset{\underset{\displaystyle O}{\downarrow}}{N}(CH_3)_2.$$

5. The composition of claim 1 wherein the perfluorocyclocarbon is a perfluorinated compound selected from the group consisting of an adamantane, substituted adamantane, [decalin, substituted decalin, bicyclononane, substituted bicyclononane,] and mixtures thereof.

6. The composition of claim 1 wherein said perfluorocyclocarbon is a solid.

7. An oxygen transfer agent liquid composition comprising water, [a major amount of] a *tricyclic or quadricyclic* perfluorocyclocarbon, and [a minor amount of] an organoamine oxide.

8. The composition of claim 6 wherein said perfluorocyclocarbon is contained in an amount of from about 10 to about 50% and said oxide is present in an amount of from about 1 to 10%.

9. The composition of claim 7 wherein said amine oxide is a polyfluoroorganoamine oxide.

10. The composition of claim 9 wherein said amine oxide is a polyfluoroamidoamine oxide.

11. The composition of claim 7 wherein the perfluorocyclocarbon is selected from a perfluorinated compound selected from the group consisting of an adamantane, substituted adamantane, [decalin, substituted decalin, bicyclononane, substituted bicyclononane,] and mixtures thereof.

12. The composition of claim 7 wherein said perfluorocyclocarbon is [selected from the group consisting of perfluoro(methylcyclohexane), perfluoro(1,3-dimethylcyclohexane), perfluoro(decahydronaphthalene), perfluoro(decahydro-1-methylnaphthalene), perfluoro(decahydrodimethylnaphthalene),] perfluorodimethyladamantane[, perfluorotrimethylbicyclo[3.3.1.]nonane, perfluorotetrahydrodicyclopentadiene, perfluorobicyclo[5.3.0.]decane and perfluorodimethylbicyclo[3.3.1.]nonane, or mixtures thereof].

13. The composition of claim 7 wherein said perfluorocyclocarbon is a mixture of perfluorodimethyladamantane and perfluorotrimethylbicyclo[3.3.1.-]nonane.

14. An artificial blood liquid composition comprising water, a *tricyclic or quadricyclic* perfluorocyclocarbon and an organoamine oxide *wherein said tricyclic or quadricyclic perfluorocyclocarbon and organoamine oxide are present in said artificial blood liquid composition in amounts which are nontoxic to an animal when said artificial blood liquid composition is infused into the animal.*

15. The composition of claim 14 wherein said perfluorocyclocarbon is contained in an amount of from about 10 to about 50% and said oxide is present in an amount of from about 1 to 10%.

16. The composition of claim 14 wherein said amine oxide is a polyfluoroorganoamine oxide.

17. The composition of claim 16 wherein said amine oxide is a polyfluoroamidoamine oxide.

18. The composition of claim 14 wherein the perfluorocyclocarbon is selected from a perfluorinated compound selected from the group consisting of an adamantane, substituted adamantane, [decalin, substituted decalin, bicyclononane, substituted bicyclononane,] and mixtures thereof.

19. The composition of claim 14 wherein said perfluorocyclocarbon is [selected from the group consisting of perfluoro(methylcyclohexane), perfluoro(1,3-dimethylcyclohexane), perfluoro(decahydronaphthalene), perfluoro(decahydro-1-methylnaphthalene), perfluoro(decahydrodimethylnaphthalene),] perfluorodimethyladamantane[, perfluorotrimethylbicyclo[3.3.1.]nonane, perfluorotetrahydrodicyclopentadiene, perfluorobicyclo[5.3.0.]decane and perfluorodimethylbicyclo[3.3.1.]nonane, or mixtures thereof].

20. The composition of claim 14 wherein said perfluorocyclocarbon is a mixture of perfluorodimethyladamantane and perfluorotrimethylbicyclo[3.3.1.-]nonane.

21. A room temperature stable artificial blood liquid composition comprising an aqueous mixture containing a [major amount of a] *tricyclic or quadricyclic* perfluorocyclocarbon and [a minor amount of] an organoamine oxide *wherein said tricyclic or quadricyclic perfluorocyclocarbon and organoamine oxide are present in said room temperature stable artificial blood liquid composition in amounts which are nontoxic to an animal when said room temperature stable artificial blood liquid composition is infused into the animal.*

22. The composition of claim 21 wherein said perfluorocyclocarbon is contained in an amount of from about 10 to about 50% and said oxide is present in an amount of from about 1 to 10%.

23. The composition of claim 21 wherein said amine oxide is a polyfluoroorganoamine oxide.

24. The composition of claim 23 wherein said amine oxide is defined by the formula

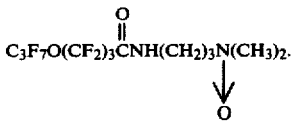

25. The composition of claim 21 wherein said perfluorocyclocarbon is [selected from the group consisting of perfluoro(methylcyclohexane), perfluoro(1,3-dimethylcyclohexane), perfluoro(decahydronaphthalene), perfluoro(decahydro-1-methylnaphthalene), perfluoro(decahydrodimethylnaphthalene),] perfluorodimethyladamantane[, perfluorotrimethylbicyclo[3.3.1.]nonane, perfluorotetrahydrodicyclopentadiene, perfluorobicyclo[5.3.0.]decane and perfluorodimethylbicyclo[3.3.1]nonane, or mixtures thereof].

26. The composition of claim 21 wherein said perfluorocyclocarbon is a mixture of perfluorodimethyladamantane and perfluorotrimethylbicyclo[3.3.1.-]nonane.

27. A room temperature stable artificial blood liquid composition comprising an aqueous mixture containing, a major amount of a perfluorocyclocarbon mixture of perfluorodimethyladamantane and perfluorotrimethylbicyclo[3.3.1.]nonane and a minor amount of a fluoroorganoamine oxide *wherein said perfluorocyclocarbon mixture and fluoroorganoamine oxide are present in said room temperature stable artificial blood liquid composition in amounts which are nontoxic to an animal when said room temperature stable artificial blood liquid composition is infused into the animal.*

28. The composition of claim 27 wherein said amine oxide is a polyfluoroamidoamine oxide.

29. The composition of claim 28 wherein said oxide defined by the formula

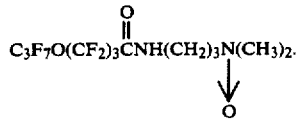

30. The composition of claim 29 wherein the perfluorocyclocarbon mixture is contained in an amount of from about 10 to 50% and the oxide is contained in an amount of from about 1 to 10% to obtain a substantially transparent liquid.

*31. The composition of claim 1 wherein said perfluorocyclocarbon is phenanthrene.*

*32. The composition of claim 7 wherein said perfluorocyclocarbon is phenanthrene.*

*33. The composition of claim 14 wherein said perfluorocyclocarbon is phenanthrene.*

*34. The composition of claim 21 wherein said perfluorocyclocarbon is phenanthrene.*

*35. A gas transport agent liquid composition containing a perfluorocyclocarbon and an organoamine oxide, said perfluorocyclocarbon is a non-aromatizable perfluorinated polycyclic compound having 9–18 carbon atoms and at least two bridgehead carbon atoms linked through a bridge containing at least one carbon atom.*

*36. A composition of claim 35 wherein said oxide is polyfluoroamidoamine oxide.*

*37. A composition of claim 36 wherein the perfluorocyclocarbon is a perfluorinated compound selected from the group consisting of an adamantane, substituted adamantane and mixtures thereof.*

*38. A composition of claim 36 wherein said perfluorocyclocarbon is contained in an amount of from about 10 to about 50% and said oxide is present in an amount of from about 1 to 10%.*

*39. An oxygen transfer agent liquid composition comprising water, a perfluorocyclocarbon and an organoamine oxide, said perfluorocyclocarbon is a non-aromatizable perfluorinated polycyclic compound having 9–18 carbon*

*atoms and at least two bridgehead carbon atoms linked through a bridge containing at least one carbon atom.*

*40. A composition of claim 39 wherein said oxide is polyfluoroamidoamine oxide.*

*41. A composition of claim 40 wherein the perfluorocyclocarbon is a perfluorinated compound selected from the group consisting of an adamantane, substituted adamantane and mixtures thereof.*

*42. A composition of claim 40 wherein said perfluorocyclocarbon is contained in an amount of from about 10 to about 50% and said oxide is present in an amount of from about 1 to 10%.*

*43. An artificial blood liquid composition comprising water, a perfluorocyclocarbon and an organoamine oxide, said perfluorocyclocarbon is a non-aromatizable perfluorinated polycyclic compound having 9–18 carbon atoms and at least two bridgehead carbon atoms linked through a bridge containing at least one carbon atom wherein said perfluorocyclocarbon and organoamine oxide are present in said artificial blood liquid composition in amounts which are nontoxic to an animal when said artificial blood liquid composition is infused into the animal.*

*44. A composition of claim 43 wherein said perfluorocyclocarbon is contained in an amount of from about 10 to about 50% and said oxide is present in an amount of from about 1 to 10%.*

*45. A composition of claim 43 wherein said oxide is a perfluoroamidoamine oxide.*

*46. A composition of claim 45 wherein the perfluorocyclocarbon is selected from a perfluorinated compound selected from the group consisting of an adamantane, substituted adamantane and mixtures thereof.*

*47. The composition of claim 35 wherein said perfluorinated compound is selected from the group consisting of bicyclononane, methylbicyclononane, trimethylbicyclo[3.3.1.]nonane, tetrahydrodicyclopentadiene, bicyclo[5.3.0.]decane and dimethylbicyclo[3.3.1.]nonane, or mixtures thereof.*

*48. The composition of claim 39 wherein said perfluorinated compound is selected from the group consisting of bicyclononane, methylbicyclononane, trimethylbicyclo[3.3.1.]nonane, tetrahydrodicyclopentadiene, bicyclo[5.3.0.]decane and dimethylbicyclo[3.3.1.]nonane, or mixtures thereof.*

*49. The composition of claim 43 wherein said perfluorinated compound is selected from the group consisting of bicyclononane, methylbicyclononane, trimethylbicyclo[3.3.1.]nonane, tetrahydrodicyclopentadiene, bicyclo[5.3.0.]decane and dimethylbicyclo[3.3.1.]nonane, or mixtures thereof.*

*50. A gas transport agent liquid composition containing a perfluorocyclocarbon and an organoamine oxide, said perfluorocyclocarbon is a perfluorinated polycyclic compound containing at least 12 carbon atoms.*

*51. A composition of claim 50 wherein said oxide is perfluoroamidoamine oxide.*

*52. A composition of claim 50 wherein said perfluorocyclocarbon is contained in an amount of from about 10 to about 50% and said oxide is present in an amount of from about 1 to 10%.*

*53. An oxygen transfer agent liquid composition comprising water, a perfluorocyclocarbon and an organoamine oxide, said perfluorocyclocarbon is a perfluorinated polycyclic compound containing at least 12 carbon atoms.*

*54. A composition of claim 53 wherein said oxide is polyfluoroamidoamine oxide.*

*55. A composition of claim 53 wherein said perfluorocyclocarbon is contained in an amount of from about 10 to about 50% and said oxide is present in an amount of from about 1 to 10%.*

*56. An artificial blood liquid composition comprising water, a perfluorocyclocarbon and an organoamine oxide, said perfluorocyclocarbon is a perfluorinated polycyclic compound containing at least 12 carbon atoms and said perfluorocyclocarbon and organoamine oxide are present in said artificial blood liquid composition in amounts which are nontoxic to an animal when said artificial blood liquid composition is infused into the animal.*

*57. A composition of claim 56 wherein said oxide is polyfluoroamidoamine oxide.*

*58. A composition of claim 56 wherein the perfluorocyclocarbon is contained in an amount of from about 10 to about 50% and said oxide is present in an amount of from about 1 to 10%.*

* * * * *